United States Patent [19]

Ayache et al.

[11] Patent Number: 5,061,493

[45] Date of Patent: Oct. 29, 1991

[54] GALENICAL FORMS OF CORTICOIDS FOR ADMINISTRATION PERLINGUALLY AND SUBLINGUALLY AND PROCESS FOR THEIR PREPARATION

[75] Inventors: Josiane Ayache; Jean-Jacques Ayache; Georges Bruttmann, all of Grenoble; Patrick Pedrali, Annecy, all of France; Serge Robert, Braine le Chateau, Belgium

[73] Assignee: Medibrevex, Grenoble, France

[21] Appl. No.: 254,602

[22] Filed: Oct. 7, 1988

[30] Foreign Application Priority Data

Oct. 8, 1987 [FR] France ............................ 87 14476

[51] Int. Cl.$^5$ ................................................ A61K 9/28
[52] U.S. Cl. .................................... 424/434; 424/435; 424/490
[58] Field of Search ................. 424/493, 490, 434, 435

[56] References Cited

U.S. PATENT DOCUMENTS

| | | | |
|---|---|---|---|
| 4,259,314 | 3/1981 | Lowey | 424/469 |
| 4,279,900 | 7/1981 | Bodor et al. | 514/887 X |
| 4,292,299 | 9/1981 | Suzuki et al. | 424/435 X |
| 4,432,966 | 2/1984 | Zeitoun et al. | 424/471 X |

FOREIGN PATENT DOCUMENTS

| | | | |
|---|---|---|---|
| 0205282 | 12/1986 | European Pat. Off. | |
| 57/118511 | 7/1982 | Japan | 424/435 |
| 1171691 | 11/1969 | United Kingdom | 424/435 |

*Primary Examiner*—Thurman K. Page
*Assistant Examiner*—Robert H. Harrison
*Attorney, Agent, or Firm*—Browdy and Neimark

[57] ABSTRACT

In these new galenical forms the corticoid is contained, in strictly controlled and reproducible amounts, in solid supports provided for an extended release of the active ingredient perlingually and sublingually.

The corticoid is preferably methylprednisolone.

The galenical forms can be prepared as follows:

dissolving the corticoid in a solvent, preparing dilutions with different concentrations, fractionating each of these dilutions into subdilutions, impregnating by multi-impregnation or fractionated impregnation a pharmaceutically acceptable solid support with each of the subdilutions, each of said impregnation stages being followed by a drying in forced air dried at a temperature not more than 35° C.

5 Claims, No Drawings

NEW GALENICAL FORMS OF CORTICOIDS FOR ADMINISTRATION PERLINGUALLY AND SUBLINGUALLY AND PROCESS FOR THEIR PREPARATION

FIELD OF THE INVENTION

This invention relates to new galenical forms of corticoids for administration perlingually and sublingually and a process for their preparation.

BACKGROUND OF THE INVENTION

After the first publications of CARRYER in 1950, numerous publications have confirmed the beneficial effects of glucocorticoids in human therapy. The glucocorticoids used are synthetic derivatives.

Corticoids are recommended especially for their anti-inflammatory effects, which allows their use in a vast field of human pathology.

Synthetic glucocorticoids have properties different from human suprarenal cortisol: a greater diffusion in tissues, and a slower hepatic metabolism which explains the lengthening of their half-life. They are classified according to the duration of their biological effects into short-action (less than 18 hours), intermediate-action (18 hours to 36 hours), and long-action (36 hours to 54 hours) glucocorticoids.

The choice of corticoid therefore is made as a function of its galenical form, its anti-inflammatory activity, its slight mineralo-corticoid activity and a short hypophyseal braking effect.

Administration of glucocorticoids in the standard way, by injection, often leads to a certain number of problems: buccopharyngeal candidoses, dermohypodermic atrophy at the point of injection, gastrointestinal troubles, metabolic diseases, osteoporosis, and risks of infection.

SUMMARY OF THE INVENTION

The inventors were able to discover, in a surprising way, that it was possible to reduce these drawbacks if these corticoids are administered perlingually and sublingually.

This perlingual and sublingual method is used because of its anatomic configuration which forms an entity relative to other elements of the buccal cavity.

Diagrammatically, the sublingual region can be described in the following way (each of the constitutive elements having useful properties in the administration of medicines introduced in this way).

Overall, the sublingual region comprises:

the lower face of the tongue, which serves as a ceiling, and is very rich in blood vessels, including veins, arteries and lymphatic vessels;

the floor of the mouth, which constitutes the lower part of the sublingual region. It is also an anatomic region which comprises many blood vessels and especially a very rich network of veins, arteries and lymphatic vessels;

the edges of the sublingual region, which are formed by the ascending parts of the inferior maxilla, the gums and teeth.

In the floor of the mouth are salivary glands, sublingual glands, which secrete saliva as soon as there is a contact with the sublingual region. By its composition, saliva actively participates in the disintegration of the pharmacologically active product present in this particular galenical form according to the invention.

Further, the histological structure shows the existence of immunocompetent cells in great number which, in some cases, will favor medicinal activity.

In comparison with the other constituents of the mouth, such as the inside of the cheeks, upper part of the tongue, the sublingual region therefore appears as a particular anatomic entity which makes it a preferred way of administration of medicine in comparison with administration of medicines by injection.

All other medicines whose decomposition occurs in the mouth are necessarily swallowed.

In the sublingual galenical form according to the invention, the activity of the product is based on its possibility of rapid absorption without swallowing. The advantage offered by this galenical form in comparison with other galenical forms used inside the buccal cavity is that the product goes into the blood, which avoids hepatic metabolism; the product therefore acts more quickly with maximum effectiveness.

The problems described above are avoided and it is thus possible to administer very small doses with a very good clinical result; absorption takes place very rapidly and equals absorption by way of an intravenous, even intramuscular, injection.

The new galenical forms of corticoids according to the invention therefore are characterized in that the corticoid is contained, in strictly controlled and reproducible amounts, in solid supports which provide for release of the active ingredient perlingually and sublingually.

This new galenical form is provided only for ambulatory treatments; it is intended for both children and adults.

DETAILED DESCRIPTION OF THE INVENTION

The process of obtaining the new galenical forms according to the invention will now be described in detail; the corticoid used as an example is methylprednisolone.

First, lyophilized products are dissolved in water to obtain a dilution at 5 mg of methylprednisolone or any other concentrations if this appears necessary. It is also possible to use the liquid form to impregnate globules directly.

The "mother" solution can be obtained with any other suitable solvent to obtain a mother solution in high concentration. For example, it is possible to use another polar solvent such as physiological serum or dilute ethyl alcohol.

It is possible, from this "mother" solution, to prepare other concentrations on demand, by using the same solvent as that used to prepare it.

The solutions in different desired concentrations are incorporated in a neutral excipient, in the present case, either saccharose or lactose, or also a mixture of both. The latter possibility is used in a particular pharmaceutical form, globule or granule.

These pharmaceutical forms are small spheres of saccharose (85%) and lactose (15%) so that 20 are required to make a gram for granules and about 200 for globules.

A gram of granules or globules therefore differ especially in total spherical surface, greater for globules since they are more numerous.

This large surface serves as impregnation support for active substances.

The globules are made by coating sugar crystals, which are progressively coated with concentric layers of saccharose and lactose.

The starting point is a graded crystallized sugar, so that 10 000 sugar crystals weigh one gram. These sugar crystals are placed in stainless steel coating turbines and subjected to a progressive coating.

Each coating cycle comprises four successive operations:

spraying of a sugar syrup on the mass in the turbine;
mixing of the mass and sprayed syrup;
powdering of the machines with a mixture of icing sugar and lactose;
drying of the mass by blowing in hot air.

The production cycle is repeated several times until globules are obtained whose weight is 50 times greater than the initial weight of the sugar crystals.

The amounts of syrup sprayed at each cycle, the concentration and temperature of the syrup, the spraying pressure, the mixing time, the amount of powdering and the drying time are perfectly coded and vary from one production stage to the next.

After each working day in the turbine, it is necessary to spread grains over the stainless steel plates at a slight thickness and to let them stay for several hours in a ventilated oven at 30°-35° to obtain grains with suitable moisture level before continuing the coating. A grading by screening is also performed daily.

It is obvious that, without going outside the scope of the invention, these globules can be replaced by powders or tablets, also adapted to perlingual or sublingual application.

These neutral globules are made active by the impregnation technique. The latter is achieved quite simply by agitating the globules in rotation in a turbine with a suitable dilution amount of the product to be impregnated; the latter is incorporated in the globules with a "spray doser" type injector.

To assure a perfect homogenization, a fractionated impregnation consisting in injecting the totality of the active product 3 to 5 times is performed.

Between each impregnation, the drying is performed by passage of forced, dried air at a temperature below 35° C.

Depending on the type of substance to be impregnated, it can be advantageous to work under a nitrogen atmosphere to guarantee that the physicochemical integrity of the active ingredient is maintained.

In the final stage, it is possible to consider coating the globule with a last sugar layer to isolate the active ingredient completely.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A solid composition for sublingual and perlingual administration of methylprednisolone, enabling rapid absorption and fast action of said methylprednisolone comprising a solid support selected from the group consisting of sacchrose, lactose, and mixtures thereof, and said methylprednisolone which releases controlled amount of said methylprednisolone in the sublingual and perlingual cavities of the mouth.

2. A composition according to claim 1 wherein said support is in divided form.

3. A composition according to claim 2 wherein the divided form of the support is a unit package.

4. A composition according to claim 1 wherein the solid support is a mixture of saccharose and lactose.

5. A solid composition for sublingual and perlingual administration of methylprednisolone, enabling rapid absorption and fast action of said methylprednisolone, comprising a solid support of 85% saccharose and 15% lactose and said methylprednisolone, which releases a controlled amount of said methylprednisoloine in the sublingual and perlingual cavities of the mouth.

* * * * *